(12) United States Patent
Beardmore

(10) Patent No.: US 6,443,012 B2
(45) Date of Patent: *Sep. 3, 2002

(54) MONITORING

(75) Inventor: Geoffrey Beardmore, Cheltenham (GB)

(73) Assignee: Smiths Industries Public Limited Company, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/283,279

(22) Filed: Apr. 1, 1999

(30) Foreign Application Priority Data

Apr. 24, 1998 (GB) ................................. 9808668

(51) Int. Cl.$^7$ ..................... G01N 29/06; G01N 29/10; G01N 29/24
(52) U.S. Cl. ..................................... 73/626
(58) Field of Search .................. 73/598, 600, 625, 73/626

(56) References Cited

U.S. PATENT DOCUMENTS

| | | | |
|---|---|---|---|
| 4,096,755 A | * | 6/1978 | Hause et al. ................. 73/598 |
| 4,122,725 A | * | 10/1978 | Thompson .................... 73/632 |
| 4,212,258 A | * | 7/1980 | Collins ........................ 73/603 |
| 4,497,210 A | | 2/1985 | Uchida et al. |
| 4,523,468 A | | 6/1985 | Deerkacs et al. |
| 4,524,620 A | * | 6/1985 | Wright et al. ................ 73/587 |
| 4,531,411 A | * | 7/1985 | Collins et al. ............... 73/603 |
| 4,537,073 A | | 8/1985 | Ooshiro et al. |
| 4,821,575 A | | 4/1989 | Fujikake et al. |
| 4,910,718 A | * | 3/1990 | Horn ........................... 367/124 |
| 5,337,289 A | * | 8/1994 | Fasching et al. ............ 367/140 |
| 5,798,458 A | * | 8/1998 | Monroe ........................ 360/5 |
| 5,911,158 A | * | 6/1999 | Henderson et al. ......... 310/328 |
| 5,948,984 A | * | 9/1999 | Hedberg ....................... 73/588 |
| 6,006,163 A | * | 12/1999 | Lichtenwalner et al. ..... 73/583 |
| 6,082,198 A | * | 7/2000 | Sabourin et al. ............. 73/633 |

FOREIGN PATENT DOCUMENTS

| | | | |
|---|---|---|---|
| DE | 2901818 | * | 1/1979 |
| JP | 61-155755 | | 7/1986 |
| JP | 149558 | * | 6/1988 |
| JP | 3-122563 | | 5/1991 |

* cited by examiner

Primary Examiner—Hezron Williams
Assistant Examiner—Rose M. Miller
(74) Attorney, Agent, or Firm—Connolly Bove Lodge & Hutz LLP

(57) ABSTRACT

An aircraft has several ultrasonic phased arrays acoustically bonded to parts of its structure to be monitored. The arrays are energized to produce an ultrasonic beam that scans the structure in two planes. A monitor receives the output from the arrays produced by reflection of energy from discontinuities within the structure. When there is a change in these outputs, the monitor signals a pilot display unit and a flight control system such that the aircraft flight envelope can be restricted to minimize damage.

11 Claims, 1 Drawing Sheet

MONITORING

BACKGROUND OF THE INVENTION

This invention relates to monitoring.

The invention is more particularly concerned with arrangements for monitoring defects caused during the life of a mechanical component, such as a component in an aircraft.

Aircraft structural components and moving components can be subject to excessive stress, which can lead to damage in the components. It is known to attach stress monitors on such components. Although these can detect stress in the components they cannot detect defects arising from such stress. Defects within a component can be monitored by ground-based equipment during periodic inspection but this does not enable defects arising during use to be detected until the next inspection. In an aircraft, a defect caused during flight could lead to catastrophic failure unless action is taken to avoid this.

BRIEF SUMMARY OF THE INVENTION

It is an object of the present invention to provide an improved monitoring system and method.

According to one aspect of the present invention there is provided a monitoring system including a component to be monitored, at least one phased acoustic array acoustically coupled with the component, and means for monitoring the output of the array during use of the component, the monitoring means being responsive to defects arising during use of the component and providing an output in accordance therewith.

The monitoring means preferably provides the output in response to a change in output from the acoustic array. The array is preferably energized to generate acoustic energy propagated into the component and may be energized to scan a beam of acoustic energy in two planes. The array may be provided by a square of PZT material diced into an array of square elements and is preferably operative at ultrasonic frequencies. The array may be bonded to the component and the system may include a plurality of arrays distributed over the component.

According to another aspect of the present invention, there is provided an aircraft including a component to be monitored, at least one acoustic array acoustically coupled with the component, and means in the aircraft for monitoring the output of the array during aircraft flight, the monitoring means being responsive to defects arising during flight and providing an output in accordance therewith.

The aircraft preferably includes a pilot display arranged to receive an output from the monitoring means. The monitoring means may be arranged to provide an output to an aircraft flight control system when the monitoring means detects a possible fault in the component, so as to limit the flight envelope of the aircraft.

According to a further aspect of the present invention there is provided a method of monitoring defects in a component during use of the component comprising the steps of acoustically coupling to the component at least one phased acoustic array, and monitoring the output of the array during use of the component so as to detect any defect arising during use of the component.

The method preferably includes the step of monitoring the output of the array for a change in output. The method preferably includes the step of energizing the acoustic array to produce a beam of acoustic energy that scans the component. The acoustic array is preferably energized to produce a beam of acoustic energy that scans the component in two planes.

An aircraft monitoring system and its method of use, in accordance with the present invention, will now be described, by way of example, with reference to the accompanying drawings.

DETAILED DESCRIPTION OF THE PREFERRED EMBODIMENT

Figure 1:
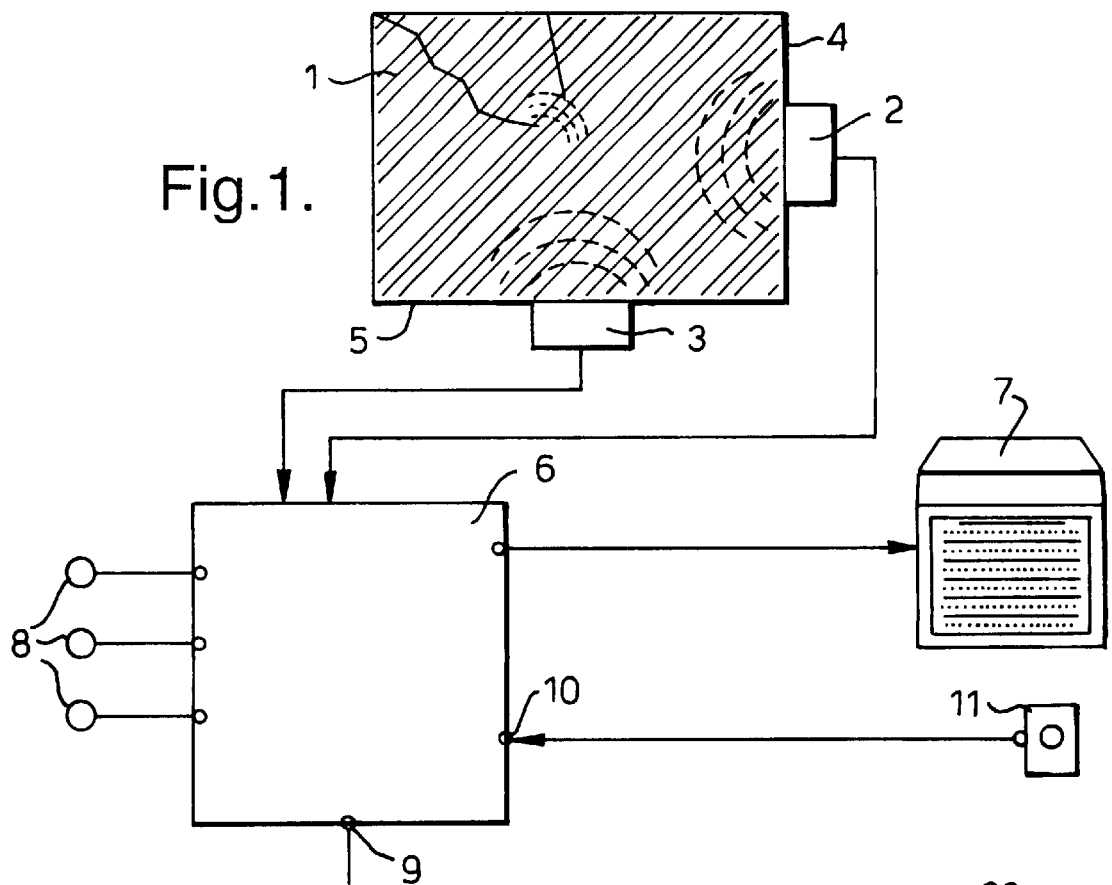
FIG. 1 is a schematic view of the system.

With reference first to FIG. 1, the system comprises an aircraft component 1 (shown in section) such as a structural beam or the like and two sensors 2 and 3 bonded to adjacent faces 4 and 5 of the component inclined at right angles to one another. The sensors 2 and 3 are bonded to the component by a material, such as an epoxy adhesive, which acoustically couples the sensor with the respective face of the component. The sensors and their wires may need to be protected from mechanical or chemical damage such as by means of a protective casing or by appropriate positioning. The sensors 2 and 3 are electrically connected with a monitor in the form of a processor unit 6, which provides outputs to a pilot's display 7 and to various flight control systems 8 within the aircraft. The processor unit 6 also has an output 9, to which ground test equipment can be connected, and has an input 10 connected to a pilot-operated control 11.

Figure 2:
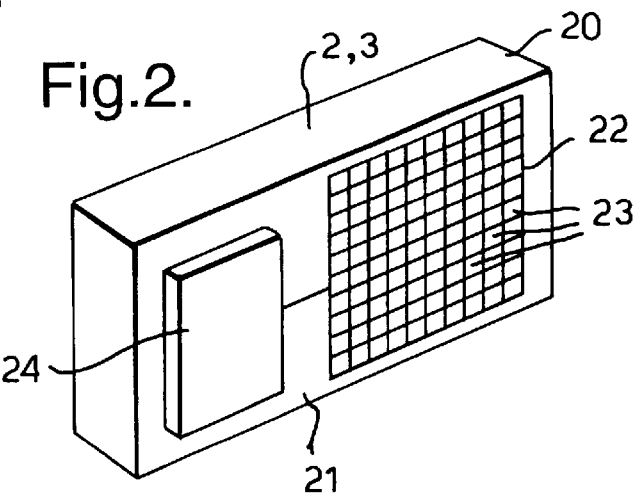
FIG. 2 is a perspective view of a scanning sensor of the system.
Figure 3:
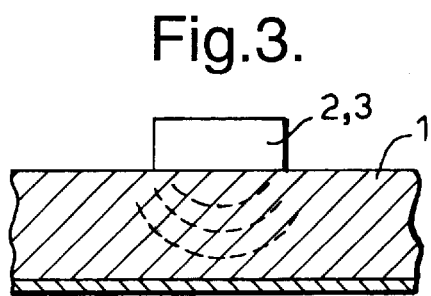
FIG. 3 shows use of the system to detect corrosion.
Figure 4:
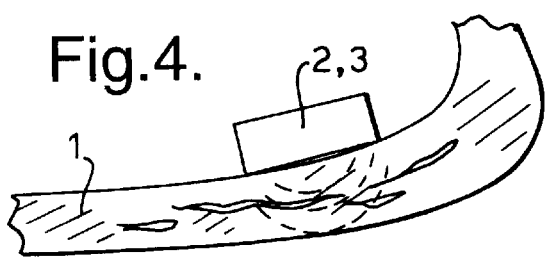
FIG. 4 shows use of the system to detect delamination.

With reference now also to FIG. 2, the sensor 2, which is identical with the other sensor 3, comprises a rectangular housing 20 with a flat front face 21 supporting a square matrix array 22 of deposited PZT material diced into an array of about ten by ten elements 23 extending in two orthogonal directions, each element being about 25 micron square. Different numbers and sizes of elements could be used. When energized, each element 23 emits pulses at ultrasonic wavelengths. The array 22 is connected to a drive unit 24 within the housing 20, which also provides signal conditioning and buffer functions. The drive unit 24 drives the array 22 in a phased manner so that it produces a beam of ultrasonic energy that scans in two planes. The power output of the array 22 may be at low levels selected so that it is insufficient to cause fatigue or other damage to the structure being monitored. The array 22 receives signals reflected back from boundaries, interfaces, imperfections, defects or other discontinuities within the component 1. The drive unit 24 of each sensor 2 and 3 is connected to the processing unit 6, which monitors the outputs from the sensors to build up a three-dimensional representation of the component 1. The data may be monitored continuously or appropriately sampled or selected according to the processing capabilities. When the processing unit 6 detects a change in the outputs of the sensors 2 and 3, it analyzes the nature of this change using image processing technology to determine its effect. If the change has a characteristic indicative of a weakening of the structure, such as a crack, or a potential future weakening, it provides an output to the pilot display 7 accordingly. The system can also respond to more gradual defects, such as caused by corrosion, as shown in FIG. 3, since the reflection from a corroded surface will generally be at a lower level or shifted in phase compared with reflections from an uncorroded surface. A gradual reduction or change in phase of a reflected signal can, therefore, be indicative of a build-up of corrosion. The system can also respond to defects on non-metallic structures, such as, for example, carbon fiber reinforced plastics or other composite materials, as shown in FIG. 4.

Delamination within such materials will produce characteristic reflections within the thickness of the material.

The display 7 preferably provides a display representation of the safe operational flight envelope for the aircraft given the nature of the detected defect. The pilot is then prompted to respond by operating the control 11, thereby signalling the processing unit 6 to provide output signals to the flight control systems 8. These output signals cause the systems 8 to limit the flight envelope of the aircraft such as to keep propagation of the defect to within acceptable limits relative to the estimated time to complete the flight. The limits on the flight envelope may be different according to the location of the detected defect. The engine revs and the rates of maneuver, for example, could be limited.

The system described enables a real-time monitoring of defects during flight of an aircraft so that any defects arising will be detected at an early stage and before they become catastrophic.

The small size of the individual elements 23 of the array 22 enables the use of relatively short wavelength ultrasonic energy, giving them a relatively high resolution, which is more suitable for relatively thin and complex sections used in airframes. Because high quality metals are generally used in airframes, there is less scattering and attenuation compared with coarse grained and cast metals used in general engineering. The effect of signal attenuation and scattering will generally be greater in composite or laminated materials but aircraft structures tend to be relatively thin and delamination failures can be expected to produce a relatively large signal.

The system may be operable in the passive mode, that is, where the sensors do not generate a signal themselves but respond to ultrasonic signals produced by the structure to which they are attached. The processor 6 can be switched to monitor for such signals. Crack propagation, in particular, can produce signals of this kind to which the system is responsive.

The system can, therefore, respond to various defects such as caused by cracks, corrosion, voids and the separation of bonded or laminated structures. It can also respond to change in shape of the structure to which it is attached, such as defects caused by distortion, yielding and excessive motion. It can also detect defects caused by battle damage and may be able to detect embrittlement.

A typical airframe might have many tens of sensors attached to structures known to be particularly subject to damage, or to structures that are particularly critical to safety. Alternatively, sensors could be distributed across the entire airframe or other system so that defects and stresses can be equalized. Sensors could be attached to moving structures, such as helicopter rotor blades, and signals supplied to and from the sensors either by slip rings or wireless telemetry. The overall data image produced by these sensors may be very complex but this need not be a problem since the system need only respond to changes in the data image, whether this be short-term or long-term.

The system is non-destructive and does not cause any significant electromagnetic emission problems. As well as being used in-flight, it can also be used for pre-flight checks and maintenance.

The sensors need not be permanently bonded to the structure being monitored, providing that there is a good acoustic coupling. This could be achieved by bolting the sensors in place and using an acoustic coupling substance to form an efficient interface between the sensor and the surface of the structure.

It will be appreciated that the invention is not confined to use in aircraft applications but could be used in other structures where it is important to be able to monitor defects, such as in marine vessels, buildings, civil engineering structures, pipelines, processing plants and the like.

What I claim is:

1. A system for monitoring defects in a solid component, the system comprising: at least one phased acoustic array; means for fixedly mounting the array to the component for acoustically coupling the array to said component; and a monitor arranged to energize said array to generate a scanned beam of acoustic energy propagated into said component and to monitor the output of said array during use of said component, wherein said monitor is responsive to defects as they arise during use of said component and provides an output in accordance therewith.

2. A monitoring system according to claim 1, wherein said monitor is arranged to energize said array to scan a beam of acoustic energy in two planes.

3. A monitoring system according to claim 1, wherein said array is provided by a square of PZT material diced into an array of square elements.

4. A monitoring system according to claim 1, wherein said array is operative at ultrasonic frequencies.

5. A monitoring system according to claim 1, wherein said array is mounted to said component by bonding to said component.

6. A monitoring system according to claim 1 including a plurality of said arrays distributed over said component.

7. A system for monitoring defects in a solid component, the system comprising: at least one phased ultrasonic array having a plurality of elements in two orthogonal directions; means for fixedly mounting the array to the component for acoustically coupling the array to said component; and a monitor for energizing said array to produce a beam of ultrasonic energy that scans the component in two planes, wherein said monitor is arranged to monitor the output of said array in response to ultrasonic energy received from said component during use of said component, and wherein said monitor is responsive to defects as they arise during use of said component and provides an output in accordance therewith.

8. A method of monitoring defects in a solid component during use of said component comprising the steps of: fixedly mounting and acoustically coupling to said component at least one phase acoustic array, energizing said array to produce a scanned beam of acoustic energy propagated into said component, and monitoring the output of said array during use of said component so as to detect any defect as they arise during use of said component.

9. A method according to claim 8, wherein the output of said array is monitored for a change in output.

10. A method according to claim 8, wherein said array is energized to produce a beam of acoustic energy that scans said component in two planes.

11. A method of monitoring defects in a solid component during use of said component comprising the steps of: fixedly mounting and acoustically coupling to said component at least one phased acoustic array, energizing said array to produce a beam of ultrasonic energy that scans said component in two planes, monitoring the output of said array produced ultrasonic energy received by said array after reflection from discontinuities in said component, and determining when said output changes in a manner indicative of change in discontinuities in said component as they arise during use of said component.

* * * * *